US011154561B2

(12) United States Patent
Shimokawa et al.

(10) Patent No.: US 11,154,561 B2
(45) Date of Patent: Oct. 26, 2021

(54) PREVENTATIVE OR THERAPEUTIC AGENT FOR PULMONARY HYPERTENSION INCLUDING CRUDE DRUG COMPONENT

(71) Applicant: TOHOKU UNIVERSITY, Miyagi (JP)

(72) Inventors: Hiroaki Shimokawa, Miyagi (JP); Kimio Satoh, Miyagi (JP); Ryo Kurosawa, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 148 days.

(21) Appl. No.: 16/325,843

(22) PCT Filed: Aug. 18, 2017

(86) PCT No.: PCT/JP2017/029685
§ 371 (c)(1),
(2) Date: May 9, 2019

(87) PCT Pub. No.: WO2018/034351
PCT Pub. Date: Feb. 22, 2018

(65) Prior Publication Data
US 2019/0262357 A1 Aug. 29, 2019

(30) Foreign Application Priority Data
Aug. 18, 2016 (JP) .............................. JP2016-160588

(51) Int. Cl.
A61K 31/56 (2006.01)
A61P 9/12 (2006.01)
A61K 9/00 (2006.01)
A61K 31/19 (2006.01)
A61P 11/00 (2006.01)
A61K 36/185 (2006.01)

(52) U.S. Cl.
CPC ............ A61K 31/56 (2013.01); A61K 9/0053 (2013.01); A61K 31/19 (2013.01); A61K 36/185 (2013.01); A61P 9/12 (2018.01); A61P 11/00 (2018.01)

(58) Field of Classification Search
CPC .................................................... A61K 31/56
See application file for complete search history.

(56) References Cited

U.S. PATENT DOCUMENTS

2015/0297670 A1 10/2015 Pagano

OTHER PUBLICATIONS

Yu et al. (Am J Hypertens (2010), vol. 23, pp. 895-903) (Year: 2010).*
Townsley et al. (Compr Physiol, (2013), vol. 2, pp. 675-709) (Year: 2013).*
Zhang et al. (Journal of Ethnopharmacology (2012), vol. 144, 195-200) (Year: 2012).*

International Search Report dated Sep. 19, 2017 in International (PCT) Application No. PCT/JP2017/029685.
Translation of International Preliminary Report on Patentability dated Sep. 19, 2017 in International (PCT) Application No. PCT/JP2017/029685.
Diebold et al., "NOX2 As a Target for Drug Development: Indications, Possible Complications, and Progress", Antioxidants & Redox Signaling, 2015, vol. 23, No. 5, pp. 375-405.
Jaquet et al., "NADPH oxidase (NOX) isoforms are inhibited by celastrol with a dual mode of action", British Journal of Pharmacology, 2011, vol. 164, pp. 507-520.
Nisbet et al., "The Role of NADPH Oxidase in Chronic Intermittent Hypoxia-Induced Pulmonary Hypertension in Mice", American Journal of Respiratory Cell and Molecular Biology, 2009, vol. 40, pp. 601-609.
Liu et al., "Hypoxic pulmonary hypertension: role of superoxide and NADPH oxidase ($gp91^{phox}$)", Am. J. Physiol. Lung. Cell. Mol, 2006, vol. 290, pages L2-L10.
Fresquet et al., "Role of reactive oxygen species and gp91phox in endothelial dysfunction of pulmonary arteries induced by chronic hypoxia", British Journal of Pharmacology, 2006, vol. 148, pp. 714-723.
Rabinovitch, "Molecular pathogenesis of pulmonary arterial hypertension", The Journal of Clinical Investigation, 2012, vol. 122, No. 12, pp. 4306-4313.
Lv et al., "Comparison of *Tripterygium wilfordii* Hook F with methotrexate in the treatment of active rheumatoid arthritis (TRIFRA): a randomised, controlled clinical trial", Annals of the Rheumatic Diseases, 2015, vol. 74, No. 6, pp. 1078-1086.
Kim et al., "Suppression of inflammatory responses by celastrol, a quinone methide triterpenoid isolated from *Celastrus regelii*", European Journal of Clinical Investigation, 2009, vol. 39, No. 9, pp. 819-827.
Allison et al., Celastrol, a Potent Antioxidant and Anti-Inflammatory Drug, as a Possible Treatment for Alzheimer's Disease", "Progress in Neuro-Psychopharmacology and Biological Psychiatry, 2001, vol. 25, No. 7, pp. 1341-1357.
Tiedemann et al., "Identification of a potent natural triterpenoid inhibitor of proteasome chymotrypsin-like activity and NF-κB with antimyeloma activity in vitro and in vivo", Blood, vol. 113, No. 17, pp. 4027-4037.
Rodiño-Janeiro et al., "Current status of NADPH oxidase research in cardiovascular pharmacology", Vascular Health and Risk Management, 2013, No. 9, pp. 401-428.
Sanders et al., "The NOX on Pulmonary Hypertension", Circulation Research, 2007, vol. 101, pp. 224-226.
Freyhaus et al., "Novel Nox inhibitor VAS2870 attenuates PDGF-dependent smooth muscle cell chemotaxis, but not proliferation", Cardiovascular Research, 2006, vol. 71, pp. 331-341.

* cited by examiner

*Primary Examiner* — Taina D Matos Negron
(74) *Attorney, Agent, or Firm* — Wenderoth, Lind & Ponack, L.L.P.

(57) ABSTRACT

A problem to be solved by the present invention is to provide a novel preventive or therapeutic agent for pulmonary hypertension containing as an active ingredient a compound that has not been known for a therapeutic effect on pulmonary hypertension heretofore. The present invention provides a preventive or therapeutic agent for pulmonary hypertension containing celastrol or a salt thereof.

3 Claims, 2 Drawing Sheets

RIGHT VENTRICULAR SYSTOLIC PRESSURE

RIGHT VENTRICLE/(LEFT VENTRICLE PLUS SEPTUM) RATIO

PREVENTATIVE OR THERAPEUTIC AGENT FOR PULMONARY HYPERTENSION INCLUDING CRUDE DRUG COMPONENT

TECHNICAL FIELD

The present invention relates to a preventive or therapeutic agent for pulmonary hypertension.

BACKGROUND ART

Pulmonary hypertension is a disease involving increased blood pressure in pulmonary arteries, which carry blood from heart to lungs, leading to impaired cardiac and pulmonary functions, and is a disease quite different from a symptom generally called "hypertension". In addition, pulmonary hypertension is a severe disease with high lethality, and hence there is an urgent need to develop a therapeutic method therefor.

Conventional treatments for pulmonary hypertension include vasodilation treatment using a catheter, and treatment such as surgical removal of thrombus, but less invasive therapeutic methods are desired. In addition, a vasodilator or the like is known as medication (e.g., Non-patent Literature 1), but there are still a large number of patients that cannot be saved by such therapeutic method. Thus, there is a strong demand for further development of a therapeutic agent for pulmonary hypertension.

CITATION LIST

Non-Patent Literature

NPL 1: J Clin Invest. 2012; 122(12): 4306-4313
NPL 2: Annals of the Rheumatic Diseases 2015 June; 74(6): 1078-86.
NPL 3: European Journal of Clinical Investigation 39(9): 819-827.
NPL 4: Progress in Neuro-Psychopharmacology and Biological Psychiatry 25(7): 1341-1357.
NPL 5: Blood 113(17): 4027-4037
NPL 6: Vascular Health and Risk Management 2013: 9 401-428
NPL 7: Circ Res. 2007; 101: 224-226
NPL 8: Cardiovascular Research 71 (2006) 331-341

SUMMARY OF INVENTION

Technical Problem

The present invention is directed to providing a novel preventive or therapeutic agent for pulmonary hypertension containing as an active ingredient a compound that has not been known for a therapeutic effect on pulmonary hypertension heretofore.

Solution to Problem

Under such circumstances, the inventors of the present invention have investigated thousands of kinds of compounds. As a result, the inventors have found that celastrol or a salt thereof serving as a crude drug ingredient suppresses excessive proliferation of pulmonary artery smooth muscle cells, which is supposed to be one of the causes for pulmonary hypertension, and has preventive and therapeutic effects on pulmonary hypertension. The present invention is based on such novel findings.

Thus, the present invention provides the following items:
Item 1. A preventive or therapeutic agent for pulmonary hypertension, including celastrol or a salt thereof.
Item 2. The preventive or therapeutic agent for pulmonary hypertension according to Item 1, wherein the preventive or therapeutic agent for pulmonary hypertension is used in a form of an orally administered agent.
Item 3-1. A method of preventing or treating pulmonary hypertension, including administering an effective dose of celastrol or a salt thereof.
Item 3-2. The method according to Item 3-1, wherein the administering includes orally administering the celastrol or the salt thereof.
Item 4-1. A use of celastrol or a salt thereof, for manufacture of a preventive or therapeutic agent for pulmonary hypertension.
Item 4-2. The use according to Item 4-1, wherein the preventive or therapeutic agent for pulmonary hypertension is an orally administered agent.
Item 5-1. Celastrol or a salt thereof, for use in prevention or treatment of pulmonary hypertension.
Item 5-2. The celastrol or the salt thereof according to Item 5-1, wherein the celastrol or the salt thereof is for use in prevention or treatment of pulmonary hypertension by oral administration.

Advantageous Effects of Invention

According to the present invention, the novel preventive or therapeutic agent for pulmonary hypertension can be provided by using celastrol, which is a compound that has not been known for a therapeutic effect on pulmonary hypertension heretofore, or a salt thereof as an active ingredient.

In this connection, celastrol serving as the active ingredient of the present invention is one of the wide variety of ingredients contained in lei gong teng (crude drug obtained by processing the root of *Tripterygium wilfordii*), which has been used as a Chinese herbal medicine. Lei gong teng has been used for treating joint pain, swelling, and inflammation, and has also been reported to be effective for patients with rheumatoid arthritis (Non-patent Literature 2). In addition, celastrol has been reported to have an anti-inflammatory action (Non-patent Literature 3), an antioxidant action (Non-patent Literature 4), and an anticancer action (Non-patent Literature 5). However, there is no previous report that lei gong teng and celastrol have preventive or therapeutic effects on pulmonary hypertension. Accordingly, the surprising effect of the present invention is unpredictable from the related art by a person skilled in the art.

BRIEF DESCRIPTION OF DRAWINGS

In FIG. 2, * represents $p<0.05$ in a t-test.

DESCRIPTION OF EMBODIMENTS

Figure 1:
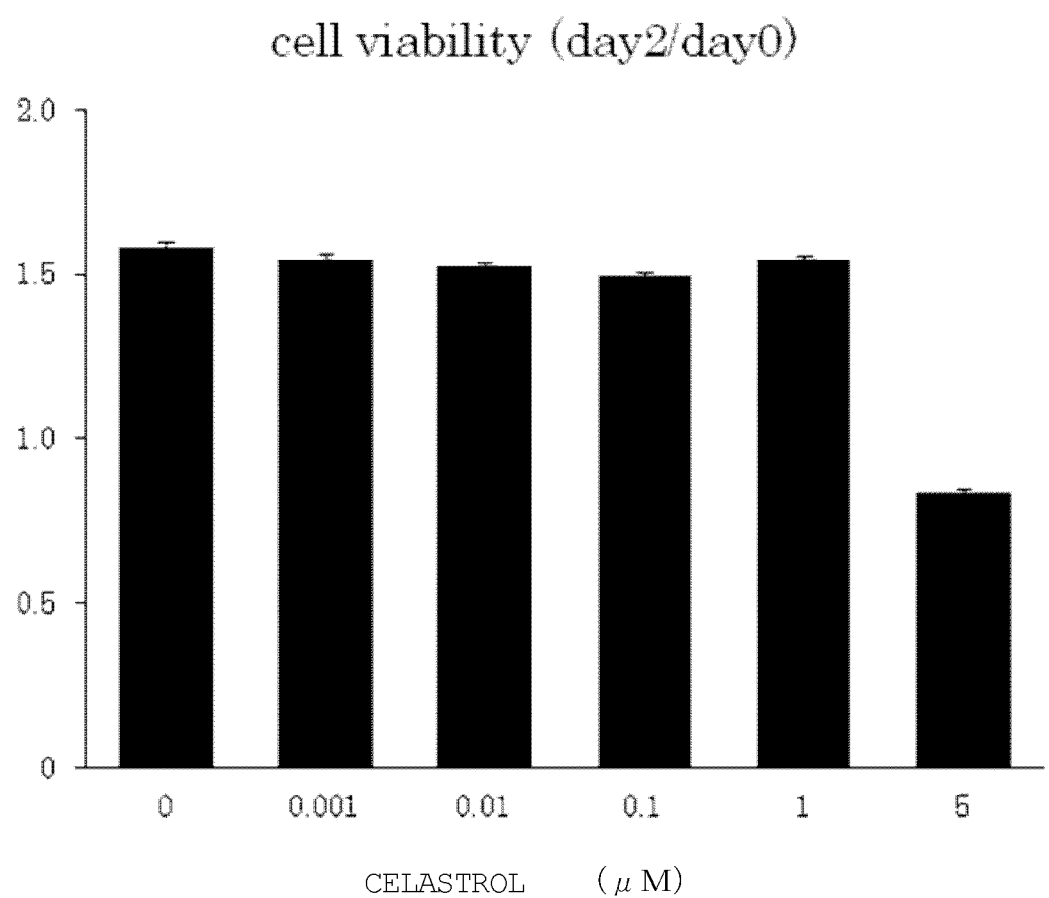
FIG. 1 is a graph for showing the results of an in vitro test in Example 1.

Preventive or Therapeutic Agent for Pulmonary Hypertension

The present invention provides a preventive or therapeutic agent for pulmonary hypertension containing celastrol or a salt thereof. Celastrol [CAS No. 34157-83-0, (tripterine: (2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicene-2-carboxylic acid] serving as an active ingredient of the present invention is a known substance having the following structure:

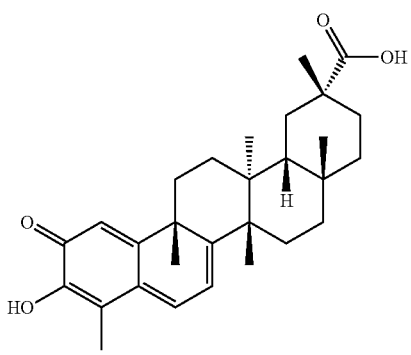

The salt of celastrol serving as the active ingredient of the present invention encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine.

Celastrol and the salt thereof serving as the active ingredient of the present invention may be present in the form of a hydrate or a solvate, and hence the compound serving as the active ingredient of the present invention also encompasses such hydrate and solvate.

A solvent forming the solvate is exemplified by alcohols, such as ethanol and propanol, organic acids, such as acetic acid, esters, such as ethyl acetate, ethers, such as tetrahydrofuran and diethyl ether, ketones, such as acetone, and dimethylformamide (DMSO).

In the present invention, celastrol or the salt thereof serving as the active ingredient of the present invention may be used alone as a preventive or therapeutic agent for pulmonary hypertension, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose, trehalose, lactose, fructose, mannitol, xylitol, and sorbitol; polyhydric alcohols, such as glycerol, polyethylene glycol, and propylene glycol; and inorganic salts, such as sodium chloride, potassium chloride, and calcium chloride.

Examples of the chelating agent include: edentates, such as disodium edetate, calcium disodium edetate, trisodium edetate, tetrasodium edetate, and calcium edetate; ethylenediaminetetraacetate; nitrilotriacetic acid or salts thereof; sodium hexametaphosphate; and citric acid.

An example of the stabilizing agent is sodium hydrogen sulfite.

Examples of the pH regulator include acids, such as hydrochloric acid, carbonic acid, acetic acid, and citric acid, and also include: alkali metal hydroxides, such as sodium hydroxide and potassium hydroxide; alkali metal carbonates or hydrogen carbonates, such as sodium carbonate; alkali metal acetates, such as sodium acetate; alkali metal citrates, such as sodium citrate; and bases, such as trometamol.

Examples of the preservative include: sorbic acid; potassium sorbate; parahydroxybenzoates, such as methyl parahydroxybenzoate, ethyl parahydroxybenzoate, propyl parahydroxybenzoate, and butyl parahydroxybenzoate; quaternary ammonium salts, such as chlorhexidine gluconate, benzalkonium chloride, benzethonium chloride, and cetylpyridinium chloride; alkylpolyaminoethylglycine; chlorobutanol; polyquad; polyhexamethylene biguanide; and chlorhexidine.

Examples of the antioxidant include sodium hydrogen sulfite, dried sodium sulfite, sodium pyrosulfite, and concentrated mixed tocopherols.

Examples of the solubilizing agent include sodium benzoate, glycerin, D-sorbitol, glucose, propylene glycol, hydroxypropyl methylcellulose, polyvinylpyrrolidone, macrogol, and D-mannitol.

Examples of the thickening agent include polyethylene glycol, methyl cellulose, ethyl cellulose, carmellose sodium, xanthan gum, sodium chondroitin sulfate, hydroxyethyl cellulose, hydroxypropyl cellulose, hydroxypropyl methylcellulose, polyvinylpyrrolidone, and polyvinyl alcohol.

In addition, the pharmaceutical composition may further contain, in addition to celastrol or the salt thereof, a compound known to have a preventive or therapeutic action on pulmonary hypertension. Examples of the compound known to have a preventive or therapeutic action on pulmonary hypertension include a prostacyclin preparation (e.g., epoprostenol), a PDE5 inhibitor (e.g., tadalafil), and an endothelin receptor antagonist (e.g., bosentan).

In addition, in the present invention, lei gong teng itself, which is a crude drug obtained by processing the root of *Tripterygium wilfordii*, or a composition obtained by adding any of the above-mentioned various carriers to the lei gong teng may be used as the preventive or therapeutic agent for pulmonary hypertension.

In the embodiment of the pharmaceutical composition, the content of celastrol or the salt thereof in the composition is not particularly limited, and may be appropriately set within, for example, conditions such as 90 mass % or more, 70 mass % or more, 50 mass % or more, 30 mass % or more, 10 mass % or more, 5 mass % or more, and 1 mass % or more in terms of the content of celastrol.

A dosage form is not particularly limited, and examples thereof may include various dosage forms including: orally administered agents, such as a tablet, a pill, a capsule, a powder, a granule, and a syrup; and parenterally administered agents, such as an injection (e.g., intravenous injection, intramuscular injection, or local injection), a gargle, a drop, external preparations (an ointment, a cream, a patch, and an inhalant), and a suppository. Of the dosage forms, for example, orally administered agents (e.g., a tablet, a pill, a capsule, a powder, a granule, and a syrup) and external preparations (e.g., an inhalant, an ointment, a cream, and a patch) are preferred.

In the present invention, the dose of celastrol or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less, more preferably 500 mg or less in terms of the dose of celastrol. The lower limit of the dose of celastrol or the salt thereof is also not particularly limited, and may be appropriately set within, for example, such a range that a daily dose for adults is generally 1 mg or more, preferably 10 mg or more, more preferably 100 mg or more in terms of the dose of celastrol. When administered once daily, celastrol or the salt thereof only needs to be contained in the above-mentioned amount in a single dose. When administered three times daily, celastrol or the salt thereof only needs to be contained in an amount corresponding to one-third of the above-mentioned amount in a single dose.

The preventive or therapeutic agent for pulmonary hypertension of the present invention is administered to patients, such as mammals. Examples of the mammals include humans, monkeys, mice, rats, rabbits, cats, dogs, pigs, cattle, horses, and sheep.

In Non-patent Literature 6, the inhibitory effects of celastrol on the activities of NADPH oxidases (NOXs), specifically NOX1, NOX2, NOX4, and NOX5 were assessed. In addition, in Non-patent Literature 7, there is a suggestion that NOXs may be involved in pulmonary hypertension.

In general, however, a wide variety of factors are often involved in the development and progress of a certain disease. Therefore, even when one factor is blocked, a desired therapeutic effect is not necessarily obtained. Accordingly, even when treatment merely using a factor known to be involved in a certain disease as a target for treating the disease is attempted, a preferred result is not necessarily obtained. In addition, a wide variety of compounds are known to have inhibitory effects on the activities of NOXs, and those compounds have different structures and functions. In actuality, in Non-patent Literature 8, there is a report of the result that vascular smooth muscle cell proliferation was not affected by a NOX inhibitor. Further, a cause for pulmonary hypertension serving as a target disease of the present invention has not been sufficiently clarified. Accordingly, the novel finding by the inventors of the present invention that celastrol or a salt thereof has been effective for prevention or treatment of pulmonary hypertension is unpredictable from the related art.

In addition, the preventive or therapeutic agent for pulmonary hypertension of the present invention prevents or treats pulmonary hypertension, in particular, pulmonary arterial hypertension or the like, by at least suppressing excessive proliferation of pulmonary artery smooth muscle cells.

Accordingly, the present invention also provides a suppressor for proliferation of pulmonary artery smooth muscle cells containing celastrol or a salt thereof. The active ingredient, dosage form, dose, and the like of the suppressor for excessive proliferation of pulmonary artery smooth muscle cells are the same as those of the preventive or therapeutic agent for pulmonary hypertension.

The present invention is more specifically described below by way of Examples. However, the present invention is not limited thereto.

EXAMPLES

Example 1

The ability of celastrol to suppress the proliferation of pulmonary artery smooth muscle cells from patients with pulmonary hypertension (IPAH-PASMCs) was assessed. Specifically, first, on day −1, 66 µl each of pulmonary artery smooth muscle cells derived from patients with idiopathic pulmonary arterial hypertension (IPAH-PASMCs) suspended in a 10% FBS medium (DMEM supplemented with 10% FBS) were seeded in a 96-well plate at 50,000 cells/ml. 24 Hours after the cell seeding (the time point was defined as day 0), 33 µl each of 0.003 µM, 0.03 µM, 0.3 µM, 3 µM, and 15 µM solutions of celastrol in 10% FBS containing 1% DMSO were added to the wells so that the final concentrations were 0.001 µM, 0.01 µM, 0.1 µM, 1 µM, and 5 µM, respectively. As a control, 33 µl of 10% FBS containing 1% DMSO was added in place of celastrol. On day 0 (immediately before the addition of celastrol), a cell viability was confirmed by performing MTT assay using CellTiter 96 (trademark) AQueous One Solution Cell Proliferation Assay (promega). Further, on day 2, i.e., 48 hours after the addition of celastrol, the MTT assay was performed again to observe a change in cell viability. Thus, a cell proliferation-suppressing effect was assessed. The results are shown in FIG. 1.

As shown in FIG. 1, it was found that a cell proliferation-suppressing effect on pulmonary artery smooth muscle cells derived from patients with idiopathic pulmonary arterial hypertension was obtained by the stimulation with celastrol for 48 hours.

Example 2

Figure 2:
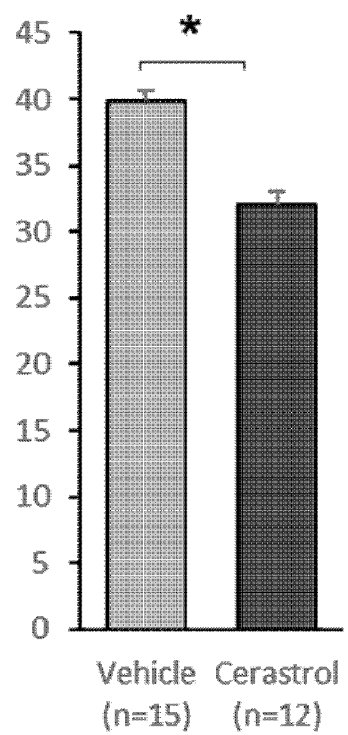
FIG. 2 are graphs for showing the influences of celastrol on a right ventricular systolic pressure and a right ventricle/(left ventricle plus septum) weight ratio in a pulmonary hypertension animal model measured in Example 2.
Figure 2:
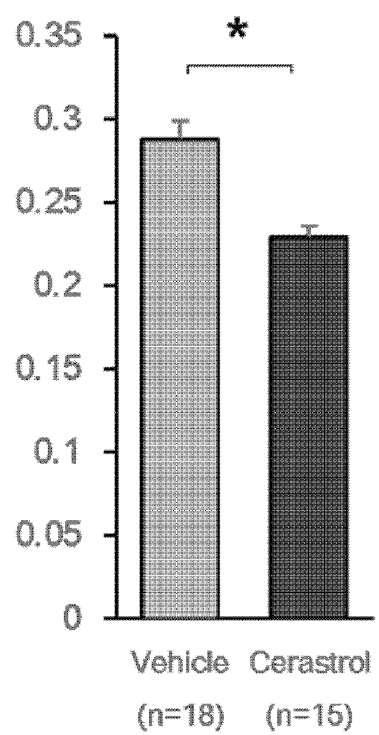

Next, the therapeutic effect of celastrol on pulmonary hypertension was assessed in vivo. Specifically, the influence of celastrol on a hypoxia-induced pulmonary hypertension mouse model was investigated. The pulmonary hypertension mouse model was generated by breeding 9-week-old male C57BL/6 mice (n=18) in a hypoxic chamber having an oxygen concentration of from 8% to 12% for 28 days. The celastrol group was intraperitoneally injected with a PBS solution, which was prepared by dissolving celastrol in DMSO and then diluting the solution with PBS so that the final DMSO concentration was 1.2%, at 1 mg/kg/2 days for 28 days from the starting day of the breeding in the hypoxic chamber. The Vehicle group was intravenously injected with the same amount of a PBS solution prepared so that the final DMSO concentration was 1.2% in place of celastrol. The mice were bred in the hypoxic chamber for 28 days and then sacrificed to measure a right ventricular systolic pressure with a pressure catheter 1.2 F (Transonic Scisense, US). In addition, after formalin fixation, the right ventricle was removed from the left ventricle to measure a right ventricle/(left ventricle plus septum) weight ratio. Then, the extent of pulmonary hypertension was assessed on the basis of those results. As shown in FIG. 2, the results were that increases in right ventricular systolic pressure and right ventricle/(left ventricle plus septum) weight ratio were suppressed in the celastrol treatment group as compared to the control group, suggesting that the development of hypoxia-induced pulmonary hypertension was suppressed.

The invention claimed is:

1. A method of treating pulmonary hypertension, comprising administering an effective dose of celastrol or a salt thereof to a subject in need thereof.

2. The method according to claim 1, wherein the celastrol or a salt thereof is administered orally.

3. The method according to claim 1, wherein the pulmonary hypertension is pulmonary arterial hypertension.

* * * * *